United States Patent
Ebdrup et al.

(10) Patent No.: US 8,946,474 B2
(45) Date of Patent: Feb. 3, 2015

(54) POLYMORPHIC FORM OF A CALCIMIMETIC COMPOUND

(75) Inventors: Søren Ebdrup, Roskilde (DK); Kim Troensegaard Nielsen, Jyllinge (DK); Tanja Maria Greve, Birkerød (DK)

(73) Assignee: LEO Pharma A/S, Ballerup (DK)

( * ) Notice: Subject to any disclaimer, the term of this patent is extended or adjusted under 35 U.S.C. 154(b) by 181 days.

(21) Appl. No.: 13/806,391

(22) PCT Filed: Jun. 24, 2011

(86) PCT No.: PCT/DK2011/000071
§ 371 (c)(1),
(2), (4) Date: Feb. 4, 2013

(87) PCT Pub. No.: WO2012/000499
PCT Pub. Date: Jan. 5, 2012

(65) Prior Publication Data
US 2013/0143846 A1  Jun. 6, 2013

Related U.S. Application Data

(60) Provisional application No. 61/360,320, filed on Jun. 30, 2010.

(51) Int. Cl.
C07C 53/00 (2006.01)
A61K 31/075 (2006.01)
A61K 31/04 (2006.01)
C07C 217/74 (2006.01)
C07C 213/10 (2006.01)
A61K 31/196 (2006.01)

(52) U.S. Cl.
CPC ............. *C07C 217/74* (2013.01); *C07C 213/10* (2013.01); *A61K 31/196* (2013.01); *C07C 2101/08* (2013.01)
USPC ............................ 562/512; 514/717; 514/740

(58) Field of Classification Search
None
See application file for complete search history.

(56) References Cited

U.S. PATENT DOCUMENTS

| 6,001,884 A | 12/1999 | Nemeth et al. |
| 2004/0242602 A1 | 12/2004 | Gungor et al. |

FOREIGN PATENT DOCUMENTS

| EP | 1203761 A2 | 5/2002 |
| EP | 1281702 A2 | 2/2003 |
| EP | 2341044 A1 | 7/2011 |
| WO | WO 93/04373 A1 | 3/1993 |
| WO | WO 94/18959 A1 | 9/1994 |
| WO | WO 95/11221 A1 | 4/1995 |
| WO | WO 96/12697 A2 | 5/1996 |
| WO | WO 97/41090 A1 | 11/1997 |
| WO | WO 98/01417 A1 | 1/1998 |
| WO | WO 00/21910 A2 | 4/2000 |
| WO | WO 01/34562 A1 | 5/2001 |
| WO | WO 01/90069 A1 | 11/2001 |
| WO | WO 02/12181 A | 2/2002 |
| WO | WO 03/099776 A1 | 12/2003 |
| WO | WO 03/099814 A1 | 12/2003 |
| WO | WO 2004/069793 A2 | 8/2004 |
| WO | WO 2004/106296 A2 | 12/2004 |
| WO | WO 2005/065050 A2 | 7/2005 |
| WO | WO 2005/115975 A1 | 12/2005 |
| WO | WO 2009/065406 A2 | 5/2009 |
| WO | WO 2010/021351 A1 | 2/2010 |

OTHER PUBLICATIONS

Balfour et al., "Cinacalcet Hydrochloride", Drugs, 65(2), 2005, pp. 271-281.
Caira, "Crystalline Polymorphism of Organic Compounds", Topics in Current Chemistry, vol. 198, 1998, pp. 163-208.
International Search Report for PCT/DK2011/000071 mailed on Sep. 5, 2011.
Lindberg et al., "Cinacalcet HCl, an Oral Calcimimetic Agent for the Treatment of Secondary Hyperparathyroidism in Hemodialysis and Peritoneal Dialysis: A Randomized, Double-Blind, Multicenter Study", J Am Soc Nephrol, vol. 16, 2005, pp. 800-807.
Soudijn et al., "Allosteric modulation of G protein-coupled receptors: perspectives and recent developments", DDT, vol. 9, No. 17, 2004, pp. 752-758.
Ureña et al., "Calcimimetic agents: Review and perspectives", Kidney International, vol. 63, Supplement 85, 2003, pp. S91-S96.
Written Opinion of the International Searching Authority for PCT/DK2011/000071 mailed on Sep. 5, 2011.

*Primary Examiner* — Jeffrey S. Lundgren
*Assistant Examiner* — Michael Schmitt
(74) *Attorney, Agent, or Firm* — Birch, Stewart, Kolasch & Birch, LLP

(57) ABSTRACT

The present invention relates to the crystalline, polymorphic Form X of the calcimimetic compound {4-[(1R,3S)-3-((R)-1-Naphthalen-1-yl-ethylamino)-cyclopentyl]-phenoxy}-acetic acid, to methods of preparation thereof, to methods of characterization thereof by single crystal X-Ray crystallography (XRC), X-Ray Powder diffractometry, attenuated total reflectance Fourier transform infrared (ATR-FTIR) spectroscopy, Solid State NMR spectroscopy and Differential Scanning Calorimetry (DSC), and to its use. The invention also relates to the preparation of Form X by crystallization from a saturated solution of {4-[(1R,3S)-3-((R)-1-Naphthalen-1-yl-ethylamino)-cyclopentyl]-phenoxy}-acetic acid in a $C_1$-$C_6$ alkyl alcohol, or alternatively by precipitation from a neutralized saponification reaction mixture following the alkaline hydrolysis of a $C_1$-$C_6$ alkyl ester of {4-[(1R,3S)-3-((R)-1-Naphthalen-1-yl-ethylamino)-cyclopentyl]-phenoxy}-acetic acid.

15 Claims, 14 Drawing Sheets

Figure 1:
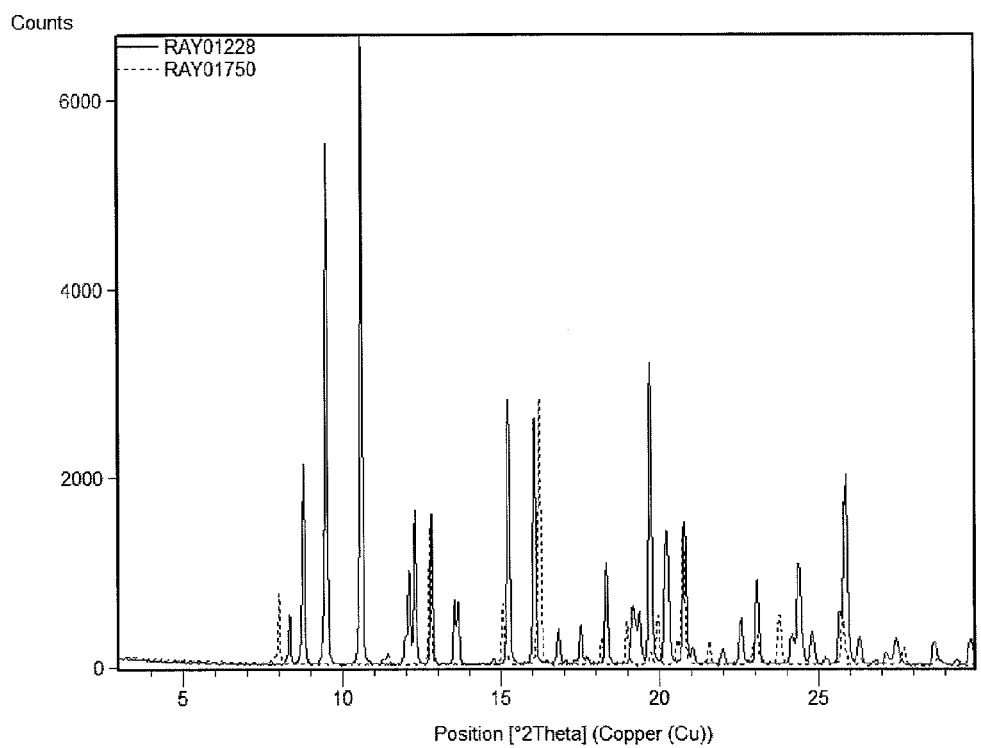

Graph 1. Comparison of the XRPD pattern of polymorph C (solid) and X (dash) of {4-[(1R,3S)-3-((R)-1-Naphthalen-1-yl-ethylamino)-cyclopentyl]-phenoxy}-acetic acid

Graph 2a. The XRPD pattern of Form C of {4-[(1R,3S)-3-((R)-1-Naphthalen-1-yl-ethylamino)-cyclopentyl]-phenoxy}-acetic acid

Graph 2b. The XRPD pattern of Form X of {4-[(1R,3S)-3-((R)-1-Naphthalen-1-yl-ethylamino)-cyclopentyl]-phenoxy}-acetic acid

Graph 3. Comparison of the DSC curves for polymorph Form C (solid) and X (dash) of {4-[(1R,3S)-3-((R)-1-Naphthalen-1-yl-ethylamino)-cyclopentyl]-phenoxy}-acetic acid

Graph 4a. The DSC (solid) and the TGA (dash) curve for polymorph Form C of {4-[(1R,3S)-3-((R)-1-Naphthalen-1-yl-ethylamino)-cyclopentyl]-phenoxy}-acetic acid

Graph 4b. The DSC (solid) and the TGA (dash) curve for polymorph Form X of {4-[(1R,3S)-3-((R)-1-Naphthalen-1-yl-ethylamino)-cyclopentyl]-phenoxy}-acetic acid

Graph 5. Comparison of the m-ATR FTIR spectra of Form C (solid) vs X (dash) of {4-[(1R,3S)-3-((R)-1-Naphthalen-1-yl-ethylamino)-cyclopentyl]-phenoxy}-acetic acid

Graph 6a. The m-ATR FTIR spectrum of Form C of {4-[(1R,3S)-3-((R)-1-Naphthalen-1-yl-ethylamino)-cyclopentyl]-phenoxy}-acetic acid.

Graph 6b. The m-ATR FTIR spectrum of Form X of {4-[(1R,3S)-3-((R)-1-Naphthalen-1-yl-ethylamino)-cyclopentyl]-phenoxy}-acetic acid

Graph 7. Comparison of the $^{13}$C-SS-NMR spectra of Form C (black) vs Form X (grey) of {4-[(1R,3S)-3-((R)-1-Naphthalen-1-yl-ethylamino)-cyclopentyl]-phenoxy}-acetic acid.

Graph 8a. The $^{13}$C-SS-NMR spectrum of Form C of {4-[(1R,3S)-3-((R)-1-Naphthalen-1-yl-ethylamino)-cyclopentyl]-phenoxy}-acetic acid

Graph 8b. The $^{13}$C-SS-NMR spectrum of Form X of {4-[(1R,3S)-3-((R)-1-Naphthalen-1-yl-ethylamino)-cyclopentyl]-phenoxy}-acetic acid

Formula 1 – Configuration of Form C of {4-[(1R,3S)-3-((R)-1-Naphthalen-1-yl-ethylamino)-cyclopentyl]-phenoxy}-acetic acid obtained by single crystal X-Ray crystallography (XRC).

Formula 2 – Configuration of Form X of {4-[(1R,3S)-3-((R)-1-Naphthalen-1-yl-ethylamino)-cyclopentyl]-phenoxy}-acetic acid obtained by single crystal X-Ray crystallography (XRC).

POLYMORPHIC FORM OF A CALCIMIMETIC COMPOUND

CROSS REFERENCE TO RELATED APPLICATIONS

This non-provisional application is a National Stage entry under U.S.C. §371 of International Application No. PCT/DK2011/000071 filed on Jun. 24, 2011, which claims the benefit of U.S. Provisional Application No. 61/360,320 filed on Jun. 30, 2010. The entire contents of all of the above applications are hereby incorporated by reference.

FIELD OF THE INVENTION

This invention relates to a novel polymorphic form of {4-[(1R,3S)-3-((R)-1-Naphthalen-1-yl-ethylamino)-cyclopentyl]-phenoxy}-acetic acid, methods of preparation thereof, and to its use.

BACKGROUND OF THE INVENTION

The invention relates to a novel polymorphic form of {4-[(1R,3S)-3-((R)-1-Naphthalen-1-yl-ethylamino)-cyclopentyl]-phenoxy}-acetic acid previously described in WO2009/065406. The compound may be used in treatment of a number of disorders or diseases associated with disturbances of CaSR activity.

Calcimimetics are small molecule allosteric activators of the calcium-sensing receptor (CaSR) [Urena, P.; Frazao, J. M. Calcimimetic agents: Review and perspectives. Kidney International (2003), 63, pp. s91-s96; Soudijn, W. et al. Allosteric modulation of G protein-coupled receptors: perspectives and recent developments. DDT (2004), 9, 752-758].

Calcimimetics have already been shown to be commercially useful for the treatment of hyperparathyroidism (HPT): The calcimimetic compound Cinacalcet® [Balfour, J. A. B. et al. Drugs (2005) 65(2), 271-281; Linberg et. al. J. Am. Soc. Nephrol (2005), 16, 800-807, Clinical Therapeutics (2005), 27(11), 1725-1751] has recently been launched for the treatment of secondary HPT in chronic kidney disease patients on dialysis and for the treatment of primary HPT in patients with parathyroid carcinoma. Thus, proof of concept for activators of calcium sensing receptor (CaSR) in humans has been achieved, and the clinical relevance is already well established. Other calcimimetic compounds were for example described in WO 94/018959, WO98/001417, WO05/065050, WO03/099814, WO03/099776, WO00/21910, WO01/34562, WO01/090069, WO97/41090, U.S. Pat. No. 6,001,884, WO96/12697, EP1203761, WO95/11221, WO93/04373, EP1281702, WO02/12181, WO04/069793, US2004242602, WO04/106296 and WO05/115975.

{4-[(1R,3S)-3-((R)-1-Naphthalen-1-yl-ethylamino)-cyclopentyl]-phenoxy}-acetic acid is part of a new promising class (WO2009/065406) of compounds displaying calcimimetic activity.

One important aspect of pharmaceutical production is the question of the physical form of the Active Pharmaceutical Ingredient (API). The physical form, such as the crystal form, of a drug substance or API used in a pharmaceutical formulation or medicament is important because different physical forms often display different fundamental properties such as solubility, dissolution rate, hygroscopicity, bioavailability, processability and stability. The existence of various solid forms, such as polymorphism or pseudopolymorphism can thereby affect the properties of the drug product.

Hence, a specific crystal form, including solvates and hydrates, might be preferable over another one. Furthermore certain forms may be preferable depending on the specific formulation and/or application. For example, the properties of a drug, such as the dissolution rate of the active ingredient, may be tuned by the proper choice of a certain crystal form, or mixtures of crystal forms in specific ratios.

A crystalline form of an API is usually preferred over a non-crystalline form, e.g. an amorphous form, in a drug formulation or during chemical processing due to its predictable properties. Crystalline forms have inter alia the advantage of greater chemical stability (pressure, heat and light), easier processability and handling. In particular the provision of a crystalline form is an important advantage during drug synthesis, especially on an industrial scale, since crystals are generally easier isolated from a reaction mixture.

Furthermore it is known that the crystallisation of a specific crystalline form of a compound in a particular solvent may result in an advantageous purification of the compound which would not be achieved by crystallisation of another form in a different solvent (partly due to differences in solubility properties of impurities in different solvents). Amorphous compounds, on the contrary, cannot be purified by recrystallisation, but will often require more expensive purification methods such as eg. preparative chromatography.

Various crystalline forms also differ in melting point, density, hardness, grinding properties, etc. and as a consequence a particular polymorphic form is preferred over another one depending on the specific application. Different crystalline forms have different stabilities in pharmaceutical formulations which depend on the excipients, vehicles, and other additives present in the dosage form. The instability of amorphous compounds or polymorphic forms which are not the most stable one represents in particular a problem when the drug substance is in suspension.

Accordingly while crystalline forms are generally preferred over non-crystalline forms of a drug substance, a specific crystalline form of a compound will be preferred depending on the various circumstances, such as its application or the process in which it is being used.

Sometimes a thermodynamically more stable form is preferred over a metastable form, sometime a metastable form which may have an increased dissolution rate is preferred.

WO2009/065406 describes the synthesis of {4-[(1R,3S)-3-(R)-1-Naphthalen-1-yl-ethylamino)-cyclopentyl]-phenoxy}-acetic acid, but does not discloses crystalline forms of the compound or the preparation of such forms. The application is silent as regards polymorphism and how to obtain a stable polymorphic form of {4-[(1R,3S)-3-((R)-1-Naphthalen-1-yl-ethylamino)-cyclopentyl]-phenoxy}-acetic acid.

WO2010/021351 describes the synthesis of {4-[(1R,3S)-3-((R)-1-Naphthalen-1-yl-ethylamino)-cyclopentyl]-phenoxy}-acetic acid derivatives but does not disclose crystalline forms of said derivatives.

SUMMARY OF THE INVENTION

The present invention surprisingly provides a stable crystalline polymorph of {4-[(1R,3S)-3-((R)-1-Naphthalen-1-yl-ethylamino)-cyclopentyl]-phenoxy}-acetic acid.

In a first aspect, the present invention thus relates to {4-[(1R,3S)-3-((R)-1-Naphthalen-1-yl-ethylamino)-cyclopentyl]-phenoxy}-acetic acid, in crystalline form.

In a preferred aspect, the present invention relates to {4-[(1R,3S)-3-((R)-1-Naphthalen-1-yl-ethylamino)-cyclopentyl]-phenoxy}-acetic acid as a crystalline polymorph exhibiting one or more of the features, or characteristic lines, shapes, or patterns depicted in Graphs 2b, 4b, 6b, 8b, Formula 2 and/or Table 1-6; or having one or more of the values listed therein, e.g. wavenumbers in cm$^{-1}$ (±3 or ±4 cm$^{-1}$ depending on the method used), or angles of reflection in degrees 2θ (±0.1); or being represented by a spectrum or diffractogram substantially similar to that shown in said Graphs or Tables, said crystalline polymorph of {4-[(1R,3S)-3-((R)-1-Naphthalen-1-yl-ethylamino)-cyclopentyl]-phenoxy}-acetic acid is hereinafter named "Form X" or "polymorph X".

Form X can be distinguished from other polymorphic forms by several analytical techniques such as X-Ray Powder Diffractometry. Graph 1 shows an overlay XRPD diffractogram of the two polymorphic forms C and X which clearly indicates both regions of similarity and difference.

In an embodiment of the present invention the Form X of {4-[(1R,3S)-3-((R)-1-Naphthalen-1-yl-ethylamino)-cyclopentyl]-phenoxy}-acetic acid is thus characterized by having an XRPD pattern essentially as shown in Graph 2b, which is an XRPD diffractogram recorded of the pure polymorphic Form X.

In another embodiment the Form X of {4-[(1R,3S)-3-((R)-1-Naphthalen-1-yl-ethylamino)-cyclopentyl]-phenoxy}-acetic acid is characterized by an XRPD pattern exhibiting one or more reflection peaks at approximately 2θ=8.0, 11.3, 11.4, 15.0, 18.2 and/or 21.5 (±0.05 degrees), (underlined is primary), respectively Form X can also be distinguished from other polymorphic forms by Differential Scanning calorimetry (DSC). Graph 3 shows an overlay thermogram of forms C and X which indicates the endothermic events for the two polymorphic forms having onsets at about 240° C. and about 255° C. (±2° C.).

In an embodiment the Form X of {4-[(1R,3S)-3-((R)-1-Naphthalen-1-yl-ethylamino)-cyclo-pentyl]-phenoxy}-acetic acid is thus characterized by having a differential scanning calorimetry (DSC) curve essentially as shown in Graph 4b comprising an endothermic event with an onset at about 255° C. (±2° C.). Graph 4b further comprises a TGA trail which indicates that {4-[(1R,3S)-3-((R)-1-Naphthalen-1-yl-ethylamino)-cyclopentyl]-phenoxy}-acetic acid is stable towards degradation at temperatures below 255° C. (±2° C.).

Form X can also be distinguished from other polymorphic forms by attenuated total reflectance Fourier transform infrared (ATR-FTIR) spectroscopy. Graph 5 shows overlay ATR-FTIR spectra of the two polymorphic forms C and X which clearly indicates both regions of similarity and difference.

In one embodiment of the present invention the Form X of {4-[(1R,3S)-3-((R)-1-Naphthalen-1-yl-ethylamino)-cyclopentyl]-phenoxy}-acetic acid is characterized by having an ATR-FTIR spectrum essentially as shown in Graph 6b, which is an ATR-FTIR spectrum recorded of the pure polymorphic Form X.

In another embodiment Form X of {4-[(1R,3S)-3-((R)-1-Naphthalen-1-yl-ethylamino)-cyclo-pentyl]-phenoxy}-acetic acid is characterized by an ATR-FTIR spectrum exhibiting one or more attenuated total reflectance peaks at approximately 1409, 1113, 1061, 939, 841, and/or 701 (±3 cm$^{-1}$) (underlined is primary), respectively.

Form X can also be distinguished from other polymorphic forms by Solid State Nuclear Magnetic Resonance (SS-NMR) spectroscopy. Graph 7 shows an overlay $^{13}$C—SS-NMR spectrum of the two polymorphic forms C and X which clearly indicates both regions of similarity and difference.

In one embodiment of the present invention Form X of {4-[(1R,3S)-3-((R)-1-Naphthalen-1-yl-ethylamino)-cyclopentyl]-phenoxy}-acetic acid is therefore characterized by having a $^{13}$C—SS-NMR spectrum essentially as shown in Graph 8b, which is the $^{13}$C—SS-NMR spectrum recorded of the pure polymorphic Form X.

In another embodiment the Form X of {4-[(1R,3S)-3-((R)-1-Naphthalen-1-yl-ethylamino)-cyclopentyl]-phenoxy}-acetic acid is characterized by a $^{13}$C—SS-NMR spectrum exhibiting one or more resonance peaks at δ$^{13}$C: 172.7, 155.8, 140.5, 68.5, 52.6, 34.0, 29.6 (±1 ppm) (underlined is primary), respectively In another embodiment of the present invention the Form C and Form X of {4-[(1R,3S)-3-((R)-1-Naphthalen-1-yl-ethylamino)-cyclopentyl]-phenoxy}-acetic acid are characterized by having single crystal parameters which are substantially the same as provided in Table 1.

TABLE 1

Single Crystal Parameters for Form C and Form X of {4-[(1R,3S)-3-((R)-1-Naphthalen-1-yl-ethylamino)-cyclopentyl]-phenoxy}-acetic acid.

| | Form X | Form C |
|---|---|---|
| Crystal system: | Orthorhombic | Tetragonal |
| Crystal description | Cube | Pyramid |
| Space Group: | P2$_1$2$_1$2$_1$ | P4$_1$2$_1$2 |
| Unit Cell Dimensions (Å) | a = 8.7299(17) | a = 10.2289(16) |
| | b = 14.822(3) | b = 10.2289(16) |
| | c = 16.353(3) | c = 41.492(13) |
| Volume (Å$^3$): | 2116.0(7) | 4341.3 (16) |
| Molecules per Unit Cell (Z) | 4 | 8 |

Throughout the present application crystal parameters such as unit cell dimensions, atomic coordinates etc are given in standard crystallographic notation, such that the standard uncertainty for a specific value is stated in brackets. For example, the value of axis a in Table 1, "a=8.7299(17)" means that there is a 95% chance that the value of a is 8.7299±0.0017 Å, i.e. lies between 8.7282 Å and 8.7316 Å.

TABLE 2

Crystal data and structure refinement details concerning the Single crystal structure determination of {4-[(1R,3S)-3-((R)-1-Naphthalen-1-yl-ethylamino)-cyclopentyl]-phenoxy}-acetic acid Form X

| | Polymorph X |
|---|---|
| Crystal data | |
| Chemical formula | C$_{25}$H$_{27}$NO$_3$ |
| M$_r$ | 389.48 |
| Crystal system, space group | Orthorhombic, P2$_1$2$_1$2$_1$ |
| Temperature (K) | 120(2) |
| a, b, c (Å) | 8.7299(17), 14.822(3), 16.353(3) |
| α, β, γ (°) | 90.00, 90.00, 90.00 |
| V (Å$^3$) | 2116.0(7) |
| Z | 4 |
| Radiation type | Mo Kα |
| μ (mm$^{-1}$) | 0.08 |
| Crystal description | Cube |
| Crystal colour | Colourless |
| Crystal size (mm) | 0.18 × 0.15 × 0.15 |
| Data collection | |
| Diffractometer | Bruker SMART platform ccd diffractometer |
| Absorption correction | — |
| No. of measured, independent and observed [I > 2σ(I)] reflections | 14231, 2719, 1946 |
| R$_{int}$ | 0.326 |
| Refinement | |
| R[F$^2$ > 2σ(F$^2$)], wR(F$^2$), S | 0.079, 0.211, 0.76 |
| No. of reflections | 5113 |

TABLE 2-continued

Crystal data and structure refinement details concerning the Single crystal structure determination of {4-[(1R,3S)-3-((R)-1-Naphthalen-1-yl-ethylamino)-cyclopentyl]-phenoxy}-acetic acid Form X

| | Polymorph X |
|---|---|
| No. of parameters | 262 |
| No. of restraints | 0 |
| H-atom treatment | H-atom parameters constrained |
| $\Delta\rho_{max}, \Delta\rho_{min}$ (e Å$^{-3}$) | 0.30, −0.52 |
| Absolute structure | Flack H D (1983), Acta Cryst. A39, 876-881 |
| Flack parameter | 4(3) |

In a presently preferred embodiment of the present invention the Form X of {4-[(1R,3S)-3-((R)-1-Naphthalen-1-yl-ethylamino)-cyclopentyl]-phenoxy}-acetic acid comprises atoms at atomic positions relative to the origin of the unit cell as set forth below in Table 3, bond lengths as set forth below in Table 4, or bond angles as set forth below in Table 5.

TABLE 3

{4-[(1R,3S)-3-((R)-1-Naphthalen-1-yl-ethylamino)-cyclopentyl]-phenoxy}-acetic acid Form X.
Atomic coordinates, equivalent isotopic displacement parameter [Å$^2$] and site occupancy factors.

| Atom | x | y | z | $U_{eq}$ | S.o.f |
|---|---|---|---|---|---|
| C1 | 0.2501(7) | 0.4585(4) | 0.4734(3) | 0.0310(14) | 1 |
| C2 | 0.3558(7) | 0.4827(4) | 0.5328(3) | 0.0410(16) | 1 |
| C3 | 0.4853(7) | 0.4279(4) | 0.5510(4) | 0.0486(17) | 1 |
| C4 | 0.5026(7) | 0.3476(4) | 0.5109(4) | 0.0414(16) | 1 |
| C5 | 0.3975(7) | 0.3185(4) | 0.4517(3) | 0.0362(14) | 1 |
| C6 | 0.4171(7) | 0.2356(4) | 0.4111(3) | 0.0388(15) | 1 |
| C7 | 0.3198(7) | 0.2086(4) | 0.3511(3) | 0.0394(15) | 1 |
| C8 | 0.1958(6) | 0.2636(3) | 0.3301(3) | 0.0334(14) | 1 |
| C9 | 0.1712(7) | 0.3442(4) | 0.3685(3) | 0.0346(14) | 1 |
| C10 | 0.2705(6) | 0.3748(3) | 0.4309(3) | 0.0303(13) | 1 |
| C11 | 0.1158(6) | 0.5197(3) | 0.4545(4) | 0.0340(14) | 1 |
| C12 | −0.0062(7) | 0.5182(4) | 0.5216(4) | 0.0448(16) | 1 |
| C13 | 0.3030(6) | 0.6357(3) | 0.3901(3) | 0.0314(13) | 1 |
| C14 | 0.3246(6) | 0.7399(3) | 0.3833(3) | 0.0333(13) | 1 |
| C15 | 0.3328(6) | 0.7596(3) | 0.2914(3) | 0.0333(13) | 1 |
| C16 | 0.2295(7) | 0.6848(4) | 0.2553(3) | 0.0418(16) | 1 |
| C17 | 0.2777(7) | 0.6010(4) | 0.3026(3) | 0.0385(15) | 1 |
| C18 | 0.2877(7) | 0.8535(4) | 0.2645(3) | 0.0330(14) | 1 |
| C19 | 0.3866(7) | 0.8999(4) | 0.2126(3) | 0.0364(14) | 1 |
| C20 | 0.3440(6) | 0.9826(3) | 0.1790(3) | 0.0349(14) | 1 |
| C21 | 0.2056(6) | 1.0197(3) | 0.1995(3) | 0.0285(13) | 1 |
| C22 | 0.1098(6) | 0.9751(4) | 0.2530(3) | 0.0317(13) | 1 |
| C23 | 0.1500(6) | 0.8926(3) | 0.2849(3) | 0.0308(13) | 1 |
| C24 | 0.2628(6) | 1.1586(3) | 0.1297(3) | 0.0364(14) | 1 |
| C25 | 0.1886(6) | 1.2464(4) | 0.1010(3) | 0.0328(13) | 1 |
| N1 | 0.1669(5) | 0.6172(3) | 0.4450(3) | 0.0318(11) | 1 |
| O1 | 0.1517(4) | 1.1013(2) | 0.1686(2) | 0.0314(9) | 1 |
| O2 | 0.0477(4) | 1.2469(3) | 0.0894(2) | 0.0361(9) | 1 |
| O3 | 0.2841(4) | 1.3089(2) | 0.0919(2) | 0.0361(10) | 1 |

TABLE 4

Bond lengths [Å] for Form X of {4-[(1R,3S)-3-((R)-1-Naphthalen-1-yl-ethylamino)-cyclopentyl]-phenoxy}-acetic acid.
Polymorph X-Bond lengths [Å]

| C1-C10 | 1.432(7) | C15-C16 | 1.546(7) |
|---|---|---|---|
| C1-C11 | 1.515(7) | C15-C18 | 1.511(7) |
| C1-C2 | 1.386(7) | C16-C17 | 1.522(7) |
| C2-C3 | 1.424(8) | C18-C19 | 1.392(7) |
| C4-C3 | 1.366(7) | C20-C19 | 1.394(7) |
| C5-C4 | 1.402(7) | C20-C21 | 1.370(7) |
| C5-C6 | 1.407(7) | C21-C22 | 1.378(7) |
| C6-C7 | 1.357(7) | C23-C18 | 1.376(7) |
| C8-C7 | 1.399(8) | C23-C22 | 1.376(7) |
| C8-C9 | 1.366(7) | C25-C24 | 1.528(7) |
| C10-C5 | 1.429(7) | N1-C11 | 1.521(6) |
| C10-C9 | 1.414(7) | N1-C13 | 1.513(6) |
| C11-C12 | 1.529(7) | O1-C21 | 1.392(6) |
| C13-C14 | 1.560(6) | O1-C24 | 1.438(6) |
| C13-C17 | 1.537(7) | O2-C25 | 1.244(6) |
| C15-C14 | 1.533(7) | O3-C25 | 1.255(6) |

TABLE 5

Bond angles [°] for Form X of {4-[(1R,3S)-3-((R)-1-Naphthalen-1-yl-ethylamino)-cyclopentyl]-phenoxy}-acetic acid.
Polymorph X-Bond angles [°]

| C1-C2-C3 | 121.8(5) | C17-C13-C14 | 106.4(4) |
|---|---|---|---|
| C1-C11-C12 | 112.6(5) | C17-C16-C15 | 103.3(4) |
| C1-C11-N1 | 111.3(4) | C18-C15-C14 | 116.7(4) |
| C2-C1-C10 | 118.8(5) | C18-C15-C16 | 113.4(4) |
| C2-C1-C11 | 120.2(5) | C18-C19-C20 | 120.6(5) |
| C3-C4-C5 | 121.8(5) | C18-C23-C22 | 120.4(5) |
| C4-C3-C2 | 118.9(6) | C19-C18-C15 | 118.1(5) |
| C4-C5-C10 | 119.4(5) | C20-C21-C22 | 119.9(5) |
| C4-C5-C6 | 121.0(5) | C20-C21-O1 | 123.9(5) |
| C5-C10-C1 | 119.2(5) | C21-C20-C19 | 119.5(5) |
| C6-C5-C10 | 119.5(5) | C21-O1-C24 | 116.5(4) |
| C6-C7-C8 | 119.3(5) | C22-C21-O1 | 116.2(5) |
| C7-C6-C5 | 121.5(5) | C23-C18-C15 | 123.0(5) |

TABLE 5-continued

Bond angles [°] for Form X of {4-[(1R,3S)-3-((R)-1-Naphthalen-1-yl-ethylamino)-cyclopentyl]-phenoxy}-acetic acid.
Polymorph X-Bond angles [°]

| | | | |
|---|---|---|---|
| C8-C9-C10 | 121.0(5) | C23-C18-C19 | 118.8(5) |
| C9-C10-C1 | 123.5(5) | C23-C22-C21 | 120.8(5) |
| C9-C10-C5 | 117.4(5) | N1-C11-C12 | 106.9(4) |
| C9-C8-C7 | 121.3(5) | N1-C13-C14 | 108.4(4) |
| C10-C1-C11 | 121.1(5) | N1-C13-C17 | 112.3(4) |
| C13-N1-C11 | 117.5(4) | O1-C24-C25 | 110.7(4) |
| C14-C15-C16 | 102.2(4) | O2-C25-C24 | 118.1(5) |
| C15-C14-C13 | 105.3(4) | O2-C25-O3 | 129.4(5) |
| C16-C17-C13 | 103.9(4) | O3-C25-C24 | 112.5(4) |

TABLE 6

Overview of the determined solubility at room temperature of polymorph Form C and X of {4-[(1R,3S)-3-((R)-1-Naphthalen-1-yl-ethylamino)-cyclopentyl]-phenoxy}-acetic acid as function of pH.

| pH | Form X Solubility (µg/ml) | Form C Solubility (µg/ml) |
|---|---|---|
| 1.0 | 1241 | 1225 |
| 2.0 | 551 | 394; 329[1] |
| 4.0 | 86 | 52; 53[1] |
| 6.0 | 78 | 43 |
| 8.0 | 80 | 55 |

[1]The solubility has been determined twice on two different batches.

In another presently preferred embodiment of the present invention the Form X of {4-[(1R,3S)-3-((R)-1-Naphthalen-1-yl-ethylamino)-cyclopentyl]-phenoxy}-acetic acid has a structure obtained by single crystal X-Ray crystallography (XRC) as shown in Formula 2.

In a further aspect the invention relates to the specific polymorphic Form X of {4-[(1R,3S)-3-((R)-1-Naphthalen-1-yl-ethylamino)-cyclopentyl]-phenoxy}-acetic acid, and processes for its preparation.

In yet another aspect, this invention relates to the manufacture of {4-[(1R,3S)-3-((R)-1-Naphthalen-1-yl-ethylamino)-cyclopentyl]-phenoxy}-acetic acid Form X using as a starting material an amorphous form of {4-[(1R,3S)-3-((R)-1-Naphthalen-1-yl-ethylamino)-cyclopentyl]-phenoxy}-acetic acid.

In a further aspect, the invention relates to the manufacture of {4-[(1R,3S)-3-((R)-1-Naphthalen-1-yl-ethylamino)-cyclopentyl]-phenoxy}-acetic acid Form X using a $C_1$-$C_6$ alkyl ester, such as a methyl ester or ethyl ester of {4-[(1R,3S)-3-((R)-1-Naphthalen-1-yl-ethylamino)-cyclopentyl]-phenoxy}-acetic acid as a starting material in a two-step, one-pot manufacturing procedure whereby the $C_1$-$C_6$ alkyl ester is hydrolyzed under alkaline conditions in $C_1$-$C_6$ alkyl alcoholic solution and the resulting product crystallized directly from the saponification reaction mixture by concentration, neutralization and dilution with water.

The invention in further aspects is directed to pharmaceutical compositions comprising this polymorphic Form X of {4-[(1R,3S)-3-((R)-1-Naphthalen-1-yl-ethylamino)-cyclopentyl]-phenoxy}-acetic acid, and to methods of its preparation and use.

DEFINITIONS

The term "$C_1$-$C_6$ linear or branched alkyl alcohols" includes methanol, ethanol, 1-propanol, 2-propanol, 1-butanol, tert-butanol, and 2-butanol.

BRIEF DESCRIPTION OF GRAPHS, FIGURES AND TABLES

FIG. 1 which shows Graph 1 as an overlay XRPD pattern of Form C and Form X.

Figure 2:
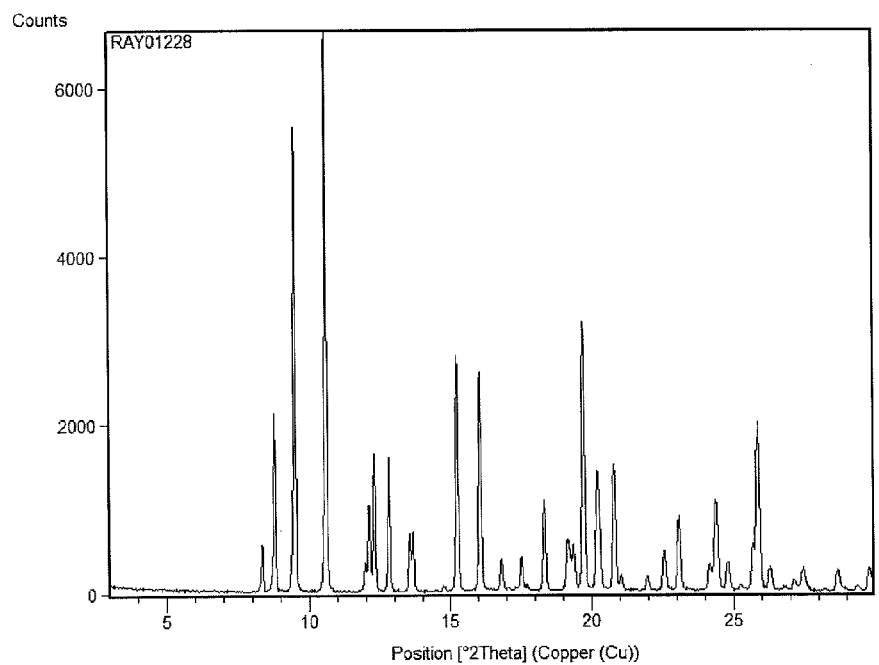

FIG. 2 which shows Graph 2a as a typical XRPD pattern of Form C.

Figure 3:
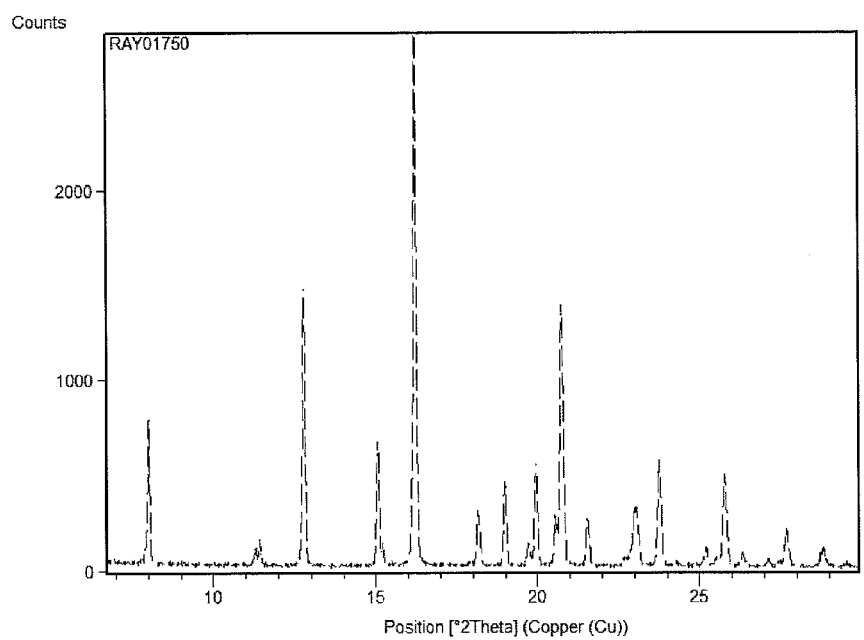

FIG. 3 which shows Graph 2b as a typical XRPD pattern of Form X.

Figure 4:
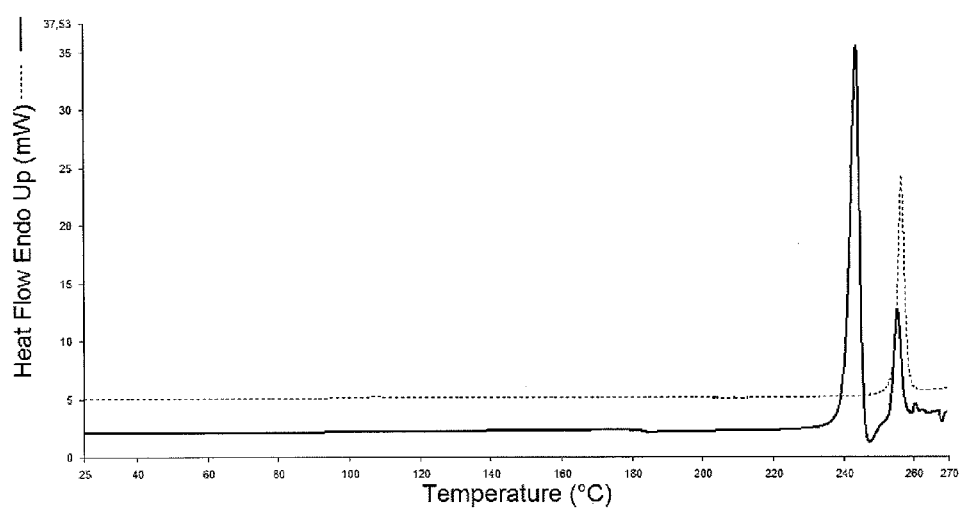

FIG. 4 which shows Graph 3 as a comparison of the DSC thermograms for Form C and Form X, which shows endothermic events for the two polymorphic forms having onsets at about 240° C. and about 255° C. (±2° C.), respectively.

Figure 5:
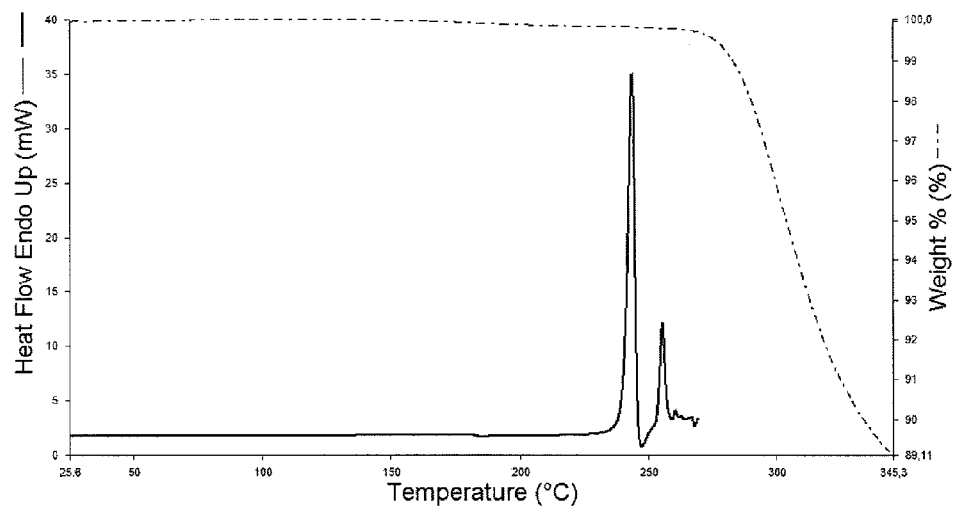

FIG. 5 which shows Graph 4a as a typical DSC+TGA thermogram for Form C.

Figure 6:
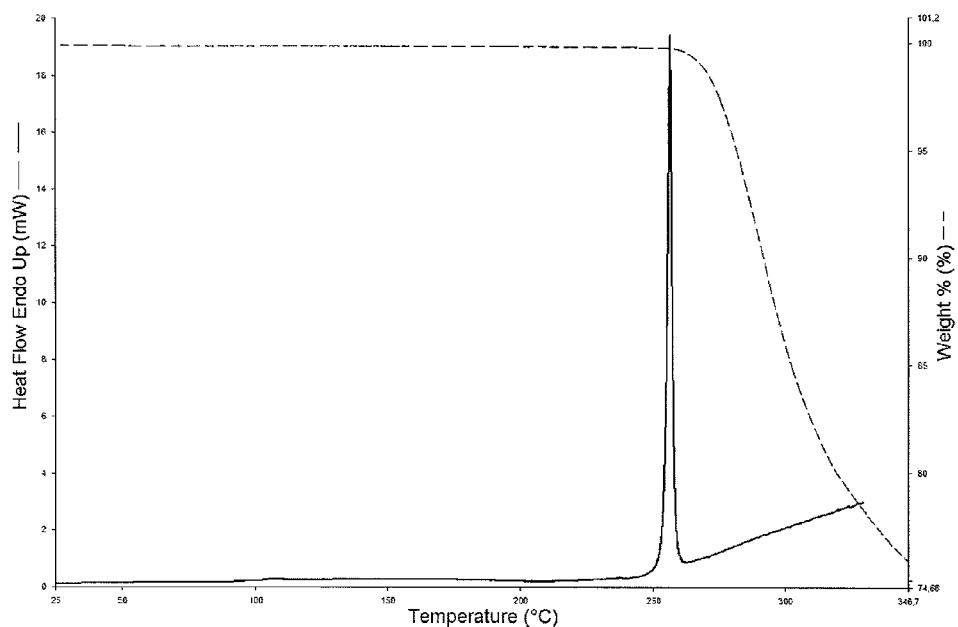

FIG. 6 which shows Graph 4b as a typical DSC+TGA thermogram for Form X.

Figure 7:
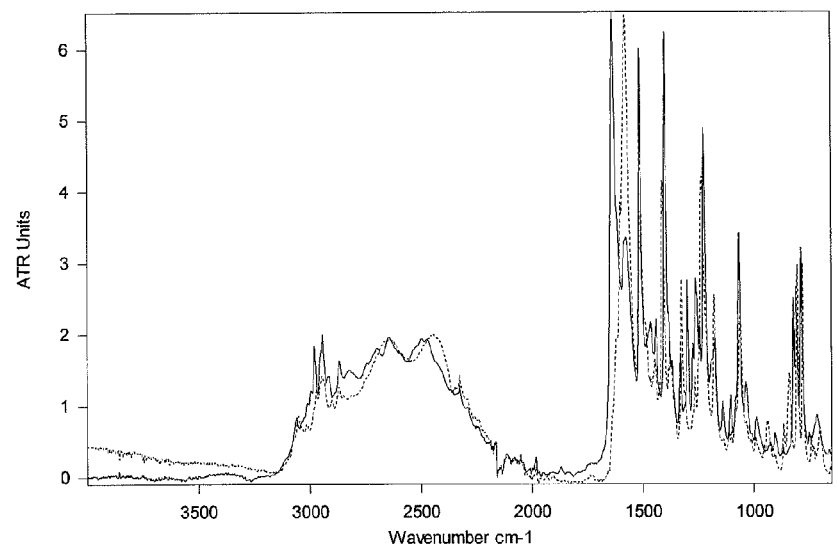

FIG. 7 which shows Graph 5 as overlay ATR-FTIR spectra of Form C and Form X.

Figure 8:
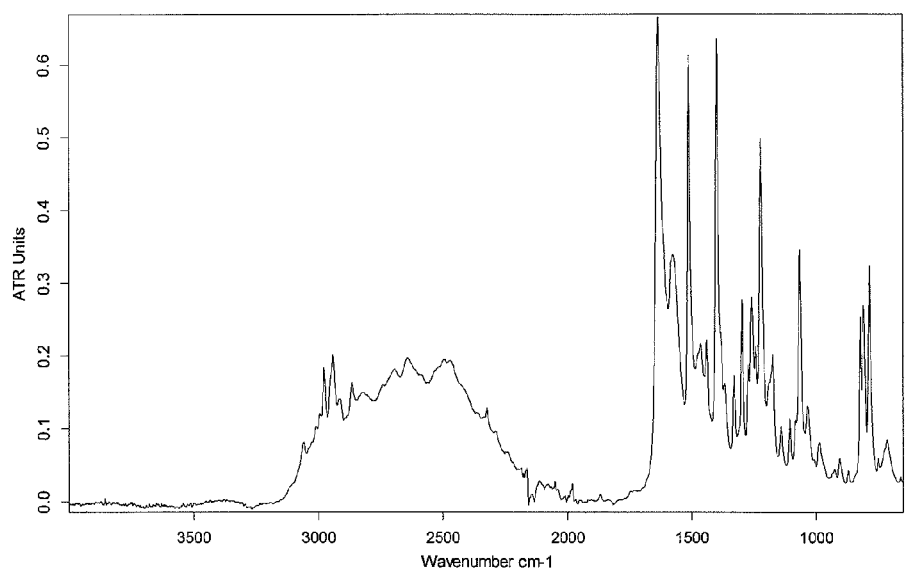

FIG. 8 which shows Graph 6a, as an ATR-FTIR spectrum recorded of the pure Form C.

Figure 9:
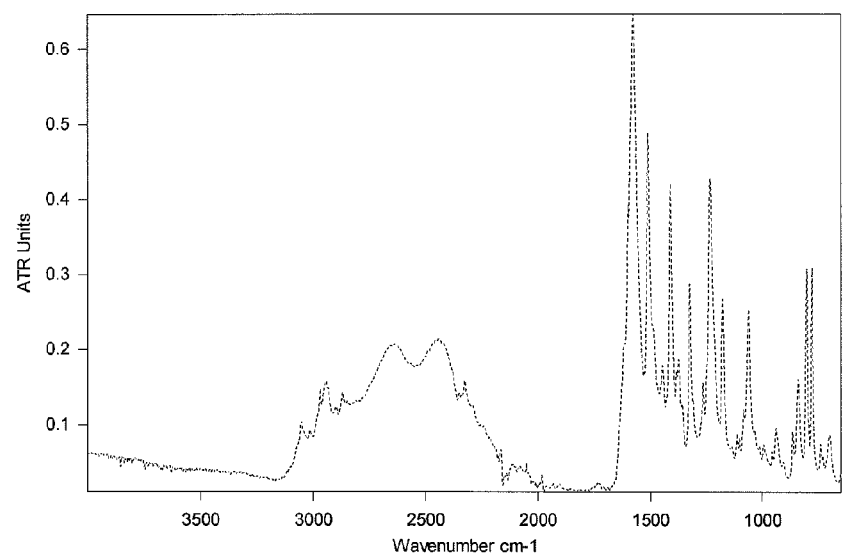

FIG. 9 which shows Graph 6b, as an ATR-FTIR spectrum recorded of the pure Form X.

Figure 10:
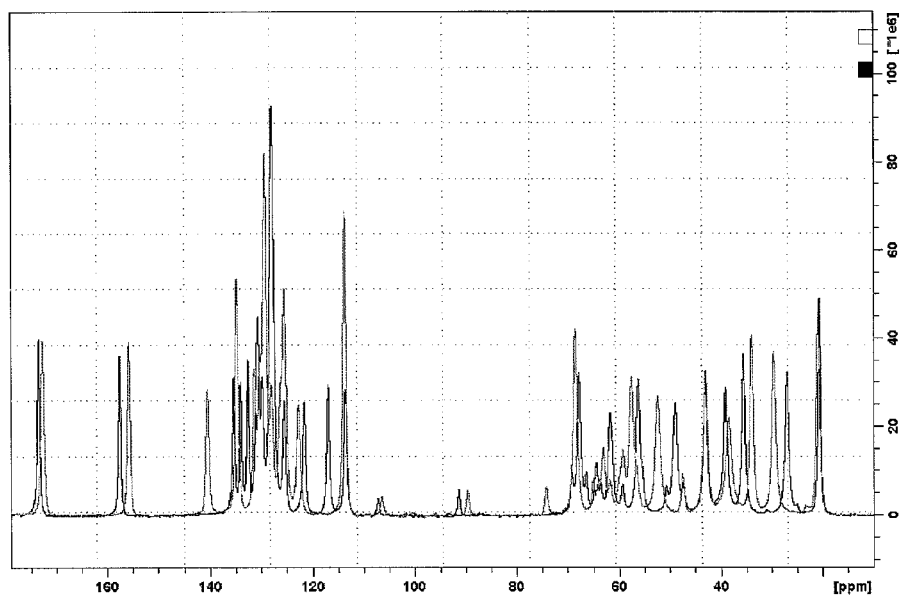

FIG. 10 which shows Graph 7, as overlay Solid State NMR spectra of Form C and Form X.

Figure 11:
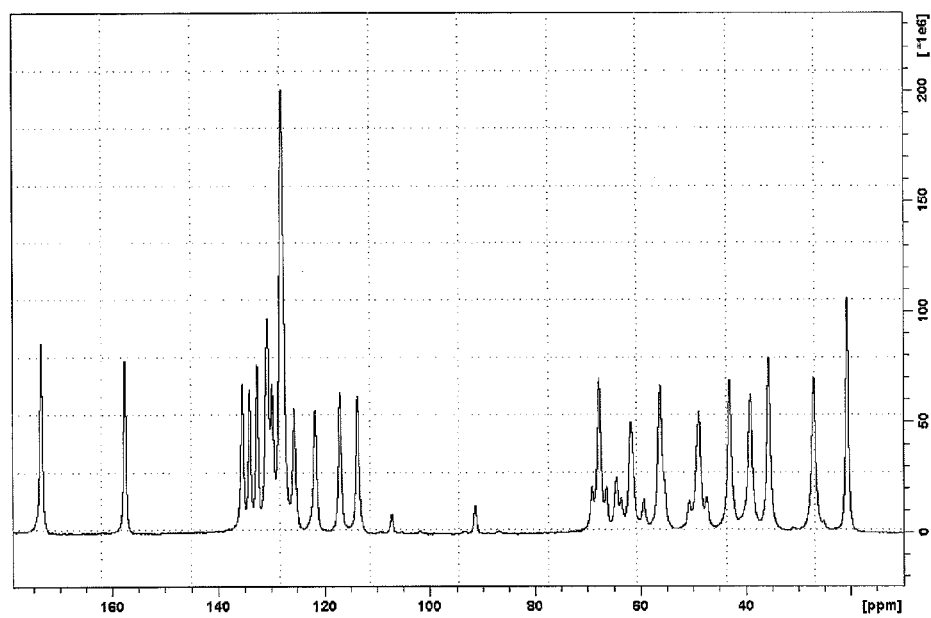

FIG. 11 which shows Graph 8a as a Solid State NMR spectrum of the pure Form C.

Figure 12:
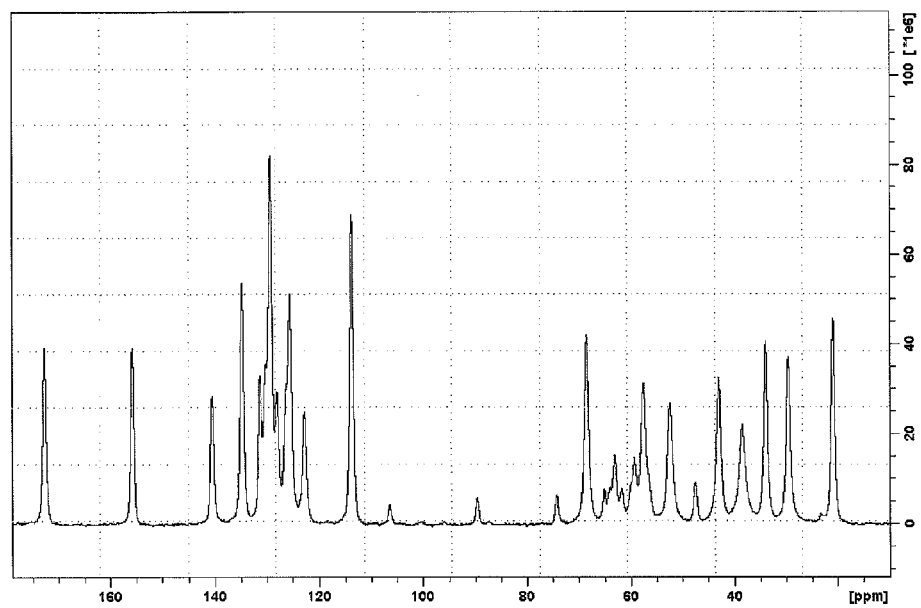

FIG. 12 which shows Graph 8b as a Solid State NMR spectrum of the pure Form X.

Figure 13:
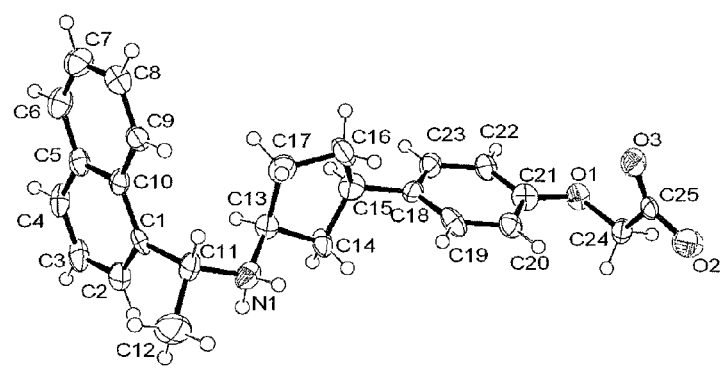

FIG. 13 which shows Formula 1 as the Single Crystal Configuration of the crystalline Form C of {4-[(1R,3S)-3-((R)-1-Naphthalen-1-yl-ethylamino)-cyclopentyl]-phenoxy}-acetic acid.

Figure 14:
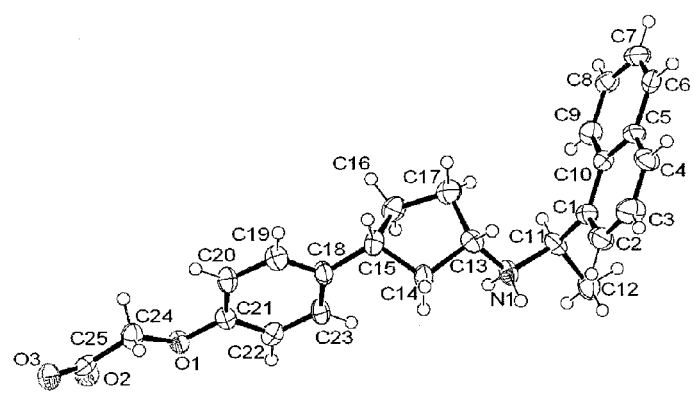

FIG. 14 which shows Formula 2 as the Single Crystal Configuration of the crystalline Form X of {4-[(1R,3S)-3-((R)-1-Naphthalen-1-yl-ethylamino)-cyclopentyl]-phenoxy}-acetic acid.

Table 1 shows the Single Crystal parameters for the crystalline Form C and Form X of {4-[(1R,3S)-3-((R)-1-Naphthalen-1-yl-ethylamino)-cyclopentyl]-phenoxy}-acetic acid.

Table 2 provides experimental details concerning the determination of the Single Crystal structure of {4-[(1R,3S)-3-((R)-1-Naphthalen-1-yl-ethylamino)-cyclopentyl]-phenoxy}-acetic acid Form X.

Table 3 provides selected atomic coordinates and isotropic thermal parameters for the Single Crystal Configuration of Form X of {4-[(1R,3S)-3-((R)-1-Naphthalen-1-yl-ethylamino)-cyclopentyl]-phenoxy}-acetic acid.

Table 4 and Table 5 provide bond lengths and bond angles, respectively, for the Single Crystal Configuration of Form X of {4-[(1R,3S)-3-((R)-1-Naphthalen-1-yl-ethylaminoycyclo-pentyl]-phenoxy}-acetic acid.

Table 6 provides solubilities at different pH for Form X and Form C of {4-[(1R,3S)-3-((R)-1-Naphthalen-1-yl-ethylamino)-cyclopentyl]-phenoxy}-acetic acid. It can be concluded that at room temperature the solubility of Form X is higher compared to Form C.

DETAILED DESCRIPTION OF THE INVENTION

{4-[(1R,3S)-3-((R)-1-Naphthalen-1-yl-ethylamino)-cyclopentyl]-phenoxy}-acetic acid is a zwitterionic molecule with pKa values of 2.9 and 9.3. Salts of the compound are not stable in formulation with a pH between the two pKa values, therefore stable crystalline forms of the zwitterionic form have been sought. Many metastable forms or solvates of {4-[(1R,3S)-3-((R)-1-Naphthalen-1-yl-ethylamino)-cyclopentyl]-phenoxy}-acetic acid have been found, but so far only two stable polymorphs have been identified (Form C and Form X). These two forms are enantiotropically related.

It is presently believed that Form X of {4-[(1R,3S)-3-((R)-1-Naphthalen-1-yl-ethylamino)-cyclopentyl]-phenoxy}-acetic acid of the present invention as described above represents a stable polymorphic crystalline form at ambient temperature, which is non-solvated and anhydrous.

A number of methods have been employed for characterizing polymorphs in pharmaceutical solids (H. G. Brittain (ed.) Polymorphism in Pharmaceutical Solids. Marcel Dekker, Inc., New York, 1999, pp. 227-278). Polarizing optical microscopy and thermomicroscopy have proven to be useful tools. Thermal analysis procedures, such as differential scanning calorimetry (DSC) and thermogravimetric analysis (TGA), can be used to obtain additional information, including phase changes, and to deduce whether each isolated form is a solvate or anhydrate. These thermal methodologies are employed to distinguish between enantiotropic and monotropic systems, as polymorphs are categorized into two types, monotropes and enantiotropes, depending upon their stability with respect to the range of temperatures and pressures.

Generally, it is possible to distinguish between monotropes and enantiotropes from their heats of fusion. An endothermic polymorphic transition indicates enantiotropes, whereas an exothermic transition indicates monotropes. Other than Differential Scanning calorimetric (DSC) analysis, there are a number of efficient ways to characterize polymorphs and distinguish one polymorph from another, as discussed hereinabove.

Crystallisation is a well known technique for the purification of chemical compounds and for obtaining a desired crystalline form of chemical compounds. However, it is known that the crystallisation of polymorphs is affected by a number of effects and the mechanism of these effects is not known and the quantitative relationship between the operational factors and the crystallisation characteristics of the polymorphs is not clearly understood.

The crystallisation process of polymorphous crystals is composed of competitive nucleation, growth, and the transformation from a metastable to a stable form. To selectively crystallise polymorphs, the mechanism of each elementary step in the crystallisation process needs to be in clear relation to the operational conditions and the key controlling factors [Crystal Growth & Design, 2004, Vol. 4, No. 6, 1153-1159].

Crystalline {4-[(1R,3S)-3-((R)-1-Naphthalen-1-yl-ethylamino)-cyclopentyl]-phenoxy}-acetic acid has proven surprisingly difficult to obtain. One obstacle has been the relative stability of the amorphous form due to a high glass transition (significantly above room temperature). Therefore if an attempt is made to precipitate {4-[(1R,3S)-3-((R)-1-Naphthalen-1-yl-ethylamino)-cyclopentyl]-phenoxy}-acetic acid too fast, the amorphous product is often obtained.

{4-[(1R,3S)-3-((R)-1-Naphthalen-1-yl-ethylamino)-cyclopentyl]-phenoxy}-acetic acid also crystallizes into many metastable forms or solvates. In many cases a solid material obtained by precipitation from a solvent has turned out to be a solvate.

Form X of {4-[(1R,3S)-3-((R)-1-Naphthalen-1-yl-ethylamino)-cyclopentyl]-phenoxy}-acetic acid can be crystallized from a blank filtered solution in a suitable solvent such as a $C_1$-$C_6$ linear or branched alkyl alcohol, like methanol, without adding seeding crystals thereby rendering Form X simpler to manufacture in large scale than other crystalline forms of {4-[(1R,3S)-3-((R)-1-Naphthalen-1-yl-ethylamino)-cyclopentyl]-phenoxy}-acetic acid.

Furthermore, it has been found that {4-[(1R,3S)-3-((R)-1-Naphthalen-1-yl-ethylamino)-cyclopentyl]-phenoxy}-acetic acid can suitably be prepared by saponification of a $C_1$-$C_6$ alkyl ester thereof in $C_1$-$C_6$ alkyl alcohol solution with aqueous alkali hydroxide such as sodium hydroxide. It has further been found that Form X of {4-[(1R,3S)-3-((R)-1-Naphthalen-1-yl-ethylamino)-cyclopentyl]-phenoxy}-acetic acid can conveniently be crystallized from the saponification mixture by concentration, pH adjustment eg. with 50% acetic acid, and dilution with water which initiates the crystallization of Form X.

In yet another aspect, this invention relates to the isolated Form X of {4-[(1R,3S)-3-((R)-1-Naphthalen-1-yl-ethylamino)-cyclopentyl]-phenoxy}-acetic acid of the present invention as defined herein which has a polymorphic purity of at least 80%, such as 81%, 82%, 83%, 84%, 85%, 86%, 87%, 88%, 89%, 90%, 91%, 92%, 93%, 94%, 95%, 96%, 97%, 98%, 99%, or 100%.

In yet another aspect, this invention relates to the isolated Form X of {4-[(1R,3S)-3-((R)-1-Naphthalen-1-yl-ethylamino)-cyclopentyl]-phenoxy}-acetic acid of the present invention as defined herein which has a degree of crystallinity of at least 80%, such as 81%, 82%, 83%, 84%, 85%, 86%, 87%, 88%, 89%, 90%, 91%, 92%, 93%, 94%, 95%, 96%, 97%, 98%, 99%, or 100%.

In yet another aspect, this invention relates to a mixture or composition of crystalline forms of {4-[(1R,3S)-3-((R)-1-Naphthalen-1-yl-ethylamino)-cyclopentyl]-phenoxy}-acetic acid, including pseudopolymorphs of {4-[(1R,3S)-3-((R)-1-Naphthalen-1-yl-ethylamino)-cyclo-pentyl]-phenoxy}-acetic acid, comprising a crystalline form of {4-[(1R,3S)-3-((R)-1-Naphthalen-1-yl-ethylamino)-cyclopentyl]-phenoxy}-acetic acid of the present invention as defined herein, such as, for example, a mixture of {4-[(1R,3S)-3-((R)-1-Naphthalen-1-yl-ethylamino)-cyclopentyl]-phenoxy}-acetic acid Form X with another polymorphic form of {4-[(1R,3S)-3-((R)-1-Naphthalen-1-yl-ethylamino)-cyclopentyl]-phenoxy}-acetic acid.

The presently preferred Form X of the present invention possesses physical properties which facilitate the manufacture of the compound, especially the readiness by which this particular crystalline polymorph can be isolated in pure form without the need for seeding with Form X crystals. Furthermore, Form X is also well-suited for long-term storage of dosage forms of the compound due to its stability towards interconversion with other solid forms of {4-[(1R,3S)-3-((R)-1-Naphthalen-1-yl-ethylamino)-cyclopentyl]-phenoxy}-acetic acid, which typically have different densities and crystal habits than Form X. Polymorphic interconversion of the API in solid dosage forms such as tablets may lead to the formation of cracks in the tablets.

Interconversion between polymorphic forms in solid dosage forms is highly problematic and therefore to be avoided if possible, which is achieved by using the stable polymorph Form X. This has been proven by stability testing; thus polymorph Form C, Form X and mixtures of the two polymorphic forms X+C have all passed the 4 week stress stability test at 60° C., 60° C./75% relative humidity and 80° C./75% relative humidity without any solid state transformation.

In yet another embodiment, the invention thus relates to the isolated Form X of {4-[(1R,3S)-3-((R)-1-Naphthalen-1-yl-ethylamino)-cyclopentyl]-phenoxy}-acetic acid which does not undergo any solid state transformation during 4 week stress stability testing at 60° C., 60° C./75% relative humidity and 80° C./75% relative humidity.

In yet another embodiment, this invention relates to the crystalline Form X of {4-[(1R,3S)-3-((R)-1-Naphthalen-1-yl-ethylamino)-cyclopentyl]-phenoxy}-acetic acid of the present invention, or to mixtures thereof with another stable crystalline polymorphic form of {4-[(1R,3S)-3-((R)-1-Naphthalen-1-yl-ethylamino)-cyclopentyl]-phenoxy}-acetic acid, as defined herein, for use in therapy.

In a specific embodiment, this invention relates to the crystalline Form X of {4-[(1R,3S)-3-((R)-1-Naphthalen-1-yl-ethylamino)-cyclopentyl]-phenoxy}-acetic acid of the present invention, or to mixtures thereof with an amorphous form of {4-[(1R,3S)-3-((R)-1-Naphthalen-1-yl-ethylamino)-cyclopentyl]-phenoxy}-acetic acid or with the crystalline Form C of {4-[(1R,3S)-3-((R)-1-Naphthalen-1-yl-ethylamino)-cyclopentyl]-phenoxy}-acetic acid as defined herein, for use in therapy.

In yet another aspect, this invention relates to a pharmaceutical composition comprising the crystalline Form X of {4-[(1R,3S)-3-((R)-1-Naphthalen-1-yl-ethylamino)-cyclopentyl]-phenoxy}-acetic acid of the present invention, or mixtures thereof with another stable crystalline polymorphic form of {4-[(1R,3S)-3-((R)-1-Naphthalen-1-yl-ethylamino)-cyclo-pentyl]-phenoxy}-acetic acid, as defined herein, together with a pharmaceutically acceptable excipient or vehicle.

In a specific embodiment, this invention relates to a pharmaceutical composition comprising the crystalline Form X of {4-[(1R,3S)-3-((R)-1-Naphthalen-1-yl-ethylamino)-cyclopentyl]-phenoxy}-acetic acid of the present invention, or mixtures thereof with the crystalline Form C of {4-[(1R,3S)-3-((R)-1-Naphthalen-1-yl-ethylamino)-cyclopentyl]-phenoxy}-acetic acid or amorphous {4-[(1R,3S)-3-((R)-1-Naphthalen-1-yl-ethylamino)-cyclopentyl]-phenoxy}-acetic acid as defined herein, or mixtures thereof, together with a pharmaceutically acceptable excipient or vehicle.

In a specific embodiment the invention provides the Form X of {4-[(1R,3S)-3-((R)-1-Naphthalen-1-yl-ethylamino)-cyclopentyl]-phenoxy}-acetic acid of the present invention, or mixtures thereof with the crystalline Form C or an amorphous form of {4-[(1R,3S)-3-((R)-1-Naphthalen-1-yl-ethylamino)-cyclopentyl]-phenoxy}-acetic acid as defined herein for use in the treatment, amelioration or prophylaxis of physiological disorders or diseases associated with disturbances of CaSR activity, such as hyperparathyroidism.

In another specific embodiment the invention provides the Form X of {4-[(R1R,3S)-3-((R)-1-Naphthalen-1-yl-ethylamino)-cyclopentyl]-phenoxy}-acetic acid of the present invention, or mixtures thereof with the crystalline Form C of {4-[(1R,3S)-3-((R)-1-Naphthalen-1-yl-ethylamino)-cyclopentyl]-phenoxy}-acetic acid as defined herein, for treating, preventing or ameliorating physiological disorders or diseases associated with disturbances of CaSR activity, such as hyperparathyroidism.

In a further embodiment the present invention is directed to the use of the preferred Form X of {4-[(1R,3S)-3-((R)-1-Naphthalen-1-yl-ethylamino)-cyclopentyl]-phenoxy}-acetic acid of the present invention, or mixtures thereof with the crystalline Form C of {4-[(R1R,3S)-3-((R)-1-Naphthalen-1-yl-ethylamino)-cyclopentyl]-phenoxy}-acetic acid as defined herein for the manufacture of a medicament for the prophylaxis, treatment or amelioration of physiological disorders or diseases associated with disturbances of CaSR activity, such as hyperparathyroidism.

In an even further embodiment the present invention is directed to a pharmaceutical composition comprising the preferred Form X of {4-[(1R,3S)-3-((R)-1-Naphthalen-1-yl-ethylamino)-cyclopentyl]-phenoxy}-acetic acid of the present invention, or mixtures thereof with the crystalline Form C of {4-[(1R,3S)-3-((R)-1-Naphthalen-1-yl-ethylamino)-cyclo-pentyl]-phenoxy}-acetic acid as defined, together with a pharmaceutically acceptable vehicle or excipient.

The present invention also provides a method of preventing, treating or ameliorating parathyroid carcinoma, parathyroid adenoma, primary parathyroid hyperplasia, cardiac, renal or intestinal disfunctions, diseases of the central nervous system, chronic renal failure, chronic kidney disease, podocyte-related diseases, primary hyperparathyroidism, secondary hyperparathyroidism, tertiary hyperparathyroidism, anemia, cardiovascular diseases, osteitis fibrosa, adynamic bone disease, osteoporosis, steroid induced osteoporosis, senile osteoporosis, post menopausal osteoporosis, osteomalacia and related bone disorders, bone loss post renal transplantation, gastrointestinal diseases, endocrine and neurodegenerative diseases, cancer, Alzheimer's disease, hypercalcemia, or renal bone diseases, which method comprising administering to a patient in need thereof an effective amount of the Form X of {4-[(1R,3S)-3-((R)-1-Naphthalen-1-yl-ethylamino)-cyclopentyl]-phenoxy}-acetic acid of the present invention, or mixtures thereof with the crystalline Form C of {4-[(1R,3S)-3-((R)-1-Naphthalen-1-yl-ethylamino)-cyclo-pentyl]-phenoxy}-acetic acid as defined herein, optionally in combination or as supplement with an active vitamin-D sterol or vitamin-D derivative, such as 1-α-hydroxycholecalciferol, ergocalciferol, cholecalciferol, 25-hydroxycholecalciferol, 1-α-25-dihydroxycholecalciferol, or in combination or as supplement with phosphate binders, estrogens, calcitonin or biphosphonates.

A presently preferred polymorph of {4-[(1R,3S)-3-((R)-1-Naphthalen-1-yl-ethylamino)-cyclopentyl]-phenoxy}-acetic acid is thus the crystalline Form X characterized by its X-Ray Powder (XRPD) Diffractogram (Graph 2b) its attenuated total reflectance Fourier transform infrared (ATR-FTIR) spectrum (Graph 6b), its differential scanning calorimetry (DSC) curve (Graph 4b), its Solid State NMR spectrum (SS-NMR) (Graph 8b), its single crystal parameters as defined in Table 1, and its crystal structure (Formula 2) obtained by single crystal X-Ray crystallography (XRC).

Another specific polymorph of {4-[(1R,3S)-3-((R)-1-Naphthalen-1-yl-ethylamino)-cyclo-pentyl]-phenoxy}-acetic acid is the crystalline Form C characterized by its X-Ray Powder (XRPD) Diffractogram (Graph 2a) its attenuated total reflectance Fourier transform infrared (ATR-FTIR) spectrum (Graph 6a), its differential scanning calorimetry (DSC) curve (Graph 4a), its Solid State NMR spectrum (SS-NMR) (Graph 8a), its single crystal parameters as defined in Table 1, and its crystal structure (Formula 1) obtained by single crystal X-Ray crystallography (XRC).

As discussed hereinabove, the crystalline composition of matter disclosed herein may be prepared from amorphous (i.e. noncrystalline) {4-[(1R,3S)-3-((R)-1-Naphthalen-1-yl-ethylamino)-cyclopentyl]-phenoxy}-acetic acid. The preparation of amorphous {4-[(1R,3S)-3-((R)-1-Naphthalen-1-yl-ethylamino)-cyclopentyl]-phenoxy}-acetic acid is disclosed in WO 2009/065406, which is incorporated herein by reference.

A specific method of forming crystalline Form X of {4-[(1R,3S)-3-((R)-1-Naphthalen-1-yl-ethylamino)-cyclopentyl]-phenoxy}-acetic acid comprises dissolving the amorphous compound in a dry solvent or solvent mixture. Preferred solvents include $C_1$-$C_6$ linear or branched alkyl alcohols such as methanol and ethanol.

Preferably, the solvent is heated, the amorphous compound dissolved in it to a point approximately equal to saturation, and the resulting solution filtered before allowing it to cool to a temperature at which the full amount of the compound dissolved is no longer soluble in the solvent, at which point crystallization commences. The crystallization is subsequently allowed to proceed, optionally with cooling of the suspension, until deemed complete. Crystals are isolated by filtration and dried, optionally in vacuo at an elevated temperature.

Another specific two-step, one-pot method of forming crystalline Form X of {4-[(1R,3S)-3-((R)-1-Naphthalen-1-yl-ethylamino)-cyclopentyl]-phenoxy}-acetic acid comprises dissolving a $C_1$-$C_6$ alkyl ester of the compound, such as a methyl or ethyl ester, in a $C_1$-$C_6$ alkyl alcohol such as ethanol followed by adding at least a molar equivalent of aqueous alkali hydroxide such as sodium hydroxide, and stirring the reaction mixture for a prolonged period such as overnight, thereby hydrolyzing the alkyl ester group.

By concentrating the hydrolysis mixture followed by pH adjustment to about 5.3 with a suitable acid such as phosphoric acid, hydrochloric acid or acetic acid followed by dilution with water, the precipitation of crystalline Form X is initiated. The crystallization is subsequently allowed to proceed, optionally with cooling of the suspension, until deemed complete. Crystals are isolated by filtration, washed and dried, optionally in vacuo at an elevated temperature.

The present invention thus in a separate embodiment provides a process for preparing crystalline Form X of {4-[(1R,3S)-3-((R)-1-Naphthalen-1-yl-ethylamino)-cyclopentyl]-phenoxy}-acetic acid which comprises either:
  a. dissolving an amorphous form of {4-[(1R,3S)-3-((R)-1-Naphthalen-1-yl-ethylamino)-cyclopentyl]-phenoxy}-acetic acid in a dry solvent or solvent mixture, preferably by heating, until an amount approximately equal to saturation has been dissolved,
  b. filtering the resulting hot solution before allowing it to cool to a temperature at which the full amount of the compound dissolved is no longer soluble in the solvent, at which point crystallization commences
  c. allowing the crystallization to proceed until deemed complete,
  d. cooling the resulting suspension of crystals and isolate the crystalline product by filtration and drying it, optionally in vacuo at an elevated temperature,
or:
  1. dissolving a $C_1$-$C_6$ alkyl ester of {4-[(1R,3S)-3-((R)-1-naphthalen-1-yl-ethyl-amino)-cyclopentyl]-phenoxy}-acetic acid in a $C_1$-$C_6$ alkyl alcohol such as methanol or ethanol, and adding at least a molar equivalent of aqueous alkali hydroxide such as sodium hydroxide,
  2. stirring the reaction mixture for a prolonged period such as overnight, preferably at room temperature,
  3. concentrating the reaction mixture in vacuo to about half volume followed by adding water to about the original volume,
  4. adjust pH to about 5.3 with 50% acetic acid and stir the resulting mixture for several hours, optionally with cooling, during which period the product slowly crystallizes,
  5. isolate the crystalline product by filtration, washing it with water and drying it, optionally in vacuo at an elevated temperature.

In a specific embodiment, the process for preparing crystalline Form X of {4-[(1R,3S)-3-((R)-1-Naphthalen-1-yl-ethylamino)-cyclopentyl]-phenoxy}-acetic acid is carried out in a solvent selected from $C_1$-$C_6$ linear or branched alkyl alcohols such as methanol.

Pharmaceutical Formulations and Methods of Treatment

For use in therapy, Form X of {4-[(1R,3S)-3-((R)-1-Naphthalen-1-yl-ethylamino)-cyclo-pentyl]-phenoxy}-acetic acid of the present invention is typically in the form of a pharmaceutical composition. The invention therefore relates to a pharmaceutical composition, both for veterinary (including mammals such as horses, cattle, sheep, pigs, dogs and cats) and for human medical use, comprising Form X of {4-[(1R,3S)-3-((R)-1-Naphthalen-1-yl-ethylamino)-cyclopentyl]-phenoxy}-acetic acid, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 10-3000 ppm by weight of the formulation, e.g. 15-2800 ppm, such as 20-2500 ppm, such as 25-2400 ppm, or 30-1000 ppm.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of compounds used in nephrology and in accordance with accepted practices such as those disclosed in *Remington: The Science and Practice of Pharmacy*, 21$^{st}$ ed., 2005, Lippincott Williams & Wilkins. In the composition of the invention, the active component may be present in an amount of from 10-3000 ppm by weight of the composition, e.g. 15-2800 ppm, such as 20-2500 ppm, such as 25-24000 ppm, or 30-1000 ppm.

For oral administration in the form of a tablet or capsule, Form X of {4-[(1R,3S)-3-((R)-1-Naphthalen-1-yl-ethylamino)-cyclopentyl]-phenoxy}-acetic acid may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, Form X of {4-[(1R,3S)-3-((R)-1-Naphthalen-1-yl-ethylamino)-cyclopentyl]-phenoxy}-acetic acid is mixed with one or more excipients, such as the ones described above, and other pharmaceutical diluents such as water to make a solid preformulation composition containing a homogenous mixture of {4-[(1R,3S)-3-((R)-1-Naphthalen-1-ykethylamino)-cyclopentyl]-phenoxy}-acetic acid. The term "homogenous" is understood to mean that Form X of {4-[(1R,3S)-3-((R)-1-Naphthalen-1-yl-ethylamino)-cyclopentyl]-phenoxy}-acetic acid is dispersed evenly throughout the composition so that the composition may readily be subdivided into equally effective unit dosage forms such as tablets or capsules. The preformulation composition may then be subdivided into unit dosage forms containing from about 0.01 to 0.1 mg Form X of {4-[(1R,3S)-3-((R)-1-Naphthalen-1-yl-ethylamino)-cyclopentyl]-phenoxy}-acetic acid.

In the form of a dosage unit, Form X of {4-[(1R,3S)-3-((R)-1-Naphthalen-1-yl-ethylamino)-cyclopentyl]-phenoxy}-acetic acid may be administered one or more times a day at appropriate intervals, always depending, however, on the condition of the patient, and in accordance with the prescription made by the medical practitioner. Conveniently, a dosage unit of a formulation contains between 0.005 mg and 0.5 mg Form X of {4-[(1R,3S)-3-((R)-1-Naphthalen-1-yl-ethylamino)-cyclopentyl]-phenoxy}-acetic acid.

A suitable dosage of Form X of {4-[(1R,3S)-3-((R)-1-Naphthalen-1-yl-ethylamino)-cyclo-pentyl]-phenoxy}-acetic acid of the invention will depend, inter alia, on the age and condition of the patient, the severity of the disease to be treated and other factors well known to the practising physician. Form X of {4-[(1R,3S)-3-((R)-1-Naphthalen-1-yl-ethylamino)-cyclopentyl]-phenoxy}-acetic acid may be administered either orally, parenterally or topically according to different dosing schedules, e.g. daily or with weekly intervals. In general a single dose will be in the range from 0.0001 to 0.001 mg/kg body weight. Form X of {4-[(1R,3S)-3-((R)-1-Naphthalen-1-yl-ethylamino)-cyclopentyl]-phenoxy}-acetic acid may be administered as a bolus (i.e. the entire daily dosis is administered at once) or in divided doses two or more times a day.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds. The administration of Form X of {4-[(1R,3S)-3-((R)-1-Naphthalen-1-yl-ethylamino)-cyclopentyl]-phenoxy}-acetic acid of the present invention with one or more other active compounds may be either concomitantly or sequentially.

Liquid formulations for either oral or parenteral administration of Form X of {4-[(1R,3S)-3-((R)-1-Naphthalen-1-yl-ethylamino)-cyclopentyl]-phenoxy}-acetic acid, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises Form X of {4-[(1R,3S)-3-((R)-1-Naphthalen-1-yl-ethylamino)-cyclopentyl]-phenoxy}-acetic acid dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, Form X of {4-[(1R,3S)-3-((R)-1-Naphthalen-1-yl-ethylamino)-cyclopentyl]-phenoxy}-acetic acid may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methylhydroxybenzoate or the like.

Compositions for rectal administration may be in the form of a suppository incorporating Form X of {4-[(1R,3S)-3-((R)-1-Naphthalen-1-yl-ethylamino)-cyclopentyl]-phenoxy}-acetic acid and a carrier such as cocoa butter, or in the form of an enema.

Compositions suitable for intra-articular administration may be in the form of a sterile aqueous preparation of Form X of {4-[(1R,3S)-3-((R)-1-Naphthalen-1-yl-ethylamino)-cyclo-pentyl]-phenoxy}-acetic acid which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. For topical administration, Form X of {4-[(1R,3S)-3-((R)-1-Naphthalen-1-yl-ethylamino)-cyclopentyl]-phenoxy}-acetic acid may typically be present in an amount of from 0.01 to 20% by weight of the composition, such as 0.1% to about 10%, but may also be present in an amount of up to about 50% of the composition.

Compositions for ophthalmic treatment may preferably additionally contain a cyclodextrin.

Compositions suitable for administration to the nasal or buccal cavity or for inhalation include powder, self-propelling and spray formulations, such as aerosols and atomizers. Such compositions may comprise Form X of {4-[(1R,3S)-3-((R)-1-Naphthalen-1-yl-ethylamino)-cyclopentyl]-phenoxy}-acetic acid in an amount of 0.01-20%, e.g. 2%, by weight of the composition.

The composition may additionally comprise one or more other active components conventionally used in the treatment of physiological disorders or diseases associated with disturbances of CaSR activity, such as hyperparathyroidism.

A further embodiment of the invention encompasses the use of Form X of {4-[(1R,3S)-3-((R)-1-Naphthalen-1-yl-ethylamino)-cyclopentyl]-phenoxy}-acetic acid as a medicament.

The present invention will be exemplified by the following non-limiting examples.

EXPERIMENTAL

Instrumentation

X-Ray Powder Diffraction (XRPD):

The diffractogram was obtained on a conventional X'pert PRO MPD diffractometer from PANalytical configured with transmission geometry and equipped with a PIXcel detector. A continuous 2θ scan range of 3-30° was used with a CuKα radiation λ=1.5418 Å source and a generator power of 40 KV and 45 mA. A 2θ step size of 0.0070°/step with a step time of 148.92 s was used. Samples were gently flattened onto a well in a 96-well plate for transmission measurements. The well plate was moved forward and backward in the x direction and all experiments were performed at room temperature.

Single-Crystal X-Ray Diffraction (XRC)

Data were collected using a Bruker SMART Apex diffractometer with a CCD area detector (Temperature: 120(2) K; Mo Ka Radiation λ=0.7107 Å; data collection method: ω/2q scans). Further details can be found in Example 4. Program(s) used to solve structure: SHELXS97 (Sheldrick, 1990); program(s) used to refine structure: SHELXL97 (Sheldrick, 1997).

ATR-FTIR Spectroscopy (Attenuated Total Reflectance Fourier Transform Infrared Spectroscopy):

The spectrum was recorded on a FTIR instrument, Equinox 55 or Tensor 27 from Bruker equipped with a GoldenGate ATR unit from SPECAC. A spectral resolution of 3 $cm^{-1}$ was used.

Differential Scanning Calorimetry (DSC):

DSC experiments were carried out using a Perkin Elmer DSC8500 system. About 0.5-3 mg of sample was used for the measurements. An aluminium pan was used for the analysis and was sealed by applying pressure by hand and pushing each part of the pan together. The temperature was ramped from −60 to 270° C. at 20° C./min. Nitrogen was used as the purge gas with a flow rate of 20 mL/min.

Thermo Gravimetric Analysis (TGA):

TGA experiments were conducted using a Perkin Elmer Pyris 1 TGA instrument. About 10-20 mg of sample was loaded into a ceramic pan for the measurements. The sample temperature was ramped from 25 to 350° C. at 10° C./min. Nitrogen was used as the purge gas at a flow rate of 40 mL/min.

Solid State Nuclear Magnetic Resonance (SS NMR):

The $^{13}C$ solid-state NMR spectrum was acquired at the Instrument Centre for Solid-State NMR spectroscopy (University of Aarhus). A Varian Unity-INOVA NMR spectrometer with a magnetic field strength of 7.04 T operating at 75.42 MHz for $^{13}C$ was used. A 5 mm homebuilt CP/MAS TLT probe using a spinning frequency of 5.0 kHz was used. The $^{13}C$ spectrum was obtained using a standard cross-polarization pulse sequence using a contact time of 1.6 ms, a relaxation delay of 4 sec, a dwell time of 10 μsec, spectral width of 50 kHz, and at ambient temperature. Proton decoupling was performed using a decoupling field strength of 95 kHz. The 5 mm $Si_3N_4$ rotor has a sample volume of 110 μl and contained approximately 100 mg substance. The spectrum was processed with zerofilling (32K real points), exponential multiplication and line broadening of 10 Hz. The spectrum was referenced to an external sample of TMS.

The given error ranges in this application for the spectroscopic characteristics, including those in the claims, may be more or less depending on factors well known to a person skilled in the art of spectroscopy and may for example depend on sample preparation, such as particle size distribution, or if the crystal form is part of a formulation, on the composition of the formulation, as well as instrumental fluctuations, and other factors.

An error range of ±5 includes, but is not limited to variations of ±5, ±4, ±3, ±2, ±1, ±0.5, ±0.4, ±0.3, ±0.2, and ±0.1; an error range of ±3 includes, but is not limited to variations of ±3, ±2, ±1, ±0.5, ±0.4, ±0.3, ±0.2, and ±0.1; an error range of ±1 includes, but is not limited to variations of ±0.9, ±0.8, ±0.7, ±0.6, ±0.5, ±0.4, ±0.3, ±0.2, and ±0.1; and an error range of ±0.2 includes, but is not limited to variations of ±0.2, ±0.15, ±0.1, ±0.09, ±0.08, ±0.07, ±0.06, ±0.05, ±0.04, ±0.03, ±0.02, and ±0.01.

Characterisation

In addition to the characterizing analyses by XRPD, XRC, DSC, ATR-FTIR and SS NMR discussed hereinabove, the solubility of {4-[(1R,3S)-3-((R)-1-Naphthalen-1-yl-ethylamino)-cyclopentyl]-phenoxy}-acetic acid Form C and X has been determined as function of pH and in MeOH. It can be concluded that at ambient temperature the solubility of Form X is higher compared to Form C (see Table 6)

Stress Stability Testing

Polymorph Form C, Form X and mixtures of the two polymorphic forms C+X have all been tested at different conditions of temperature and relative humidity for signs of solid state transformation. The stress stability test was carried out at three sets of conditions: 60° C., 60° C./75% relative humidity and 80° C./75% relative humidity, and samples were analyzed after 1, 2 and 4 weeks, i.e. after 7, 14 and 28 days.

One 1.8 ml amber screw top vial (27267-U, Supelco) containing between 50 and 100 mg {4-[(1R,3S)-3-((R)-1-Naphthalen-1-yl-ethylamino)-cyclopentyl]-phenoxy}-acetic acid was tested per individual set of conditions. The vials to be tested at 60° C. were closed with a PTFE lined black polypropylene solid cap (27416, Supelco) and placed in a thermostated heating cabinet. The vials to be tested at 60° C./75% relative humidity and 80° C./75% relative humidity were placed uncapped in a desiccator containing a saturated NaCl solution. The desiccator was subsequently placed in a thermostatted heating cabinet.

The samples were analyzed at 1, 2 and 4 weeks for
1. Visual appearance
2. HPLC assay and impurities
3. Polymorph characterization All the tested samples passed the 4 week stress stability test at 60° C., 60° C./75% relative humidity and 80'C/75% relative humidity without any solid state transformation.

PREPARATIVE EXAMPLES

Example 1

Preparation of amorphous {4-[(1R,3S)-3-((R)-1-naphthalen-1-ylethylamino)-cyclopentyl]-phenoxy}-acetic acid Step 1: {4-[(1R,3S)-3-((R)-1-naphthalen-1-yl-ethylamino)-cyclopentyl]-phenoxy}-acetic acid ethyl ester

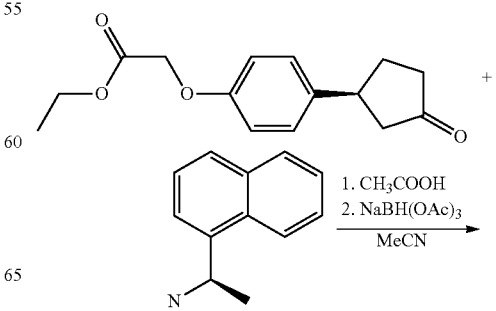

-continued

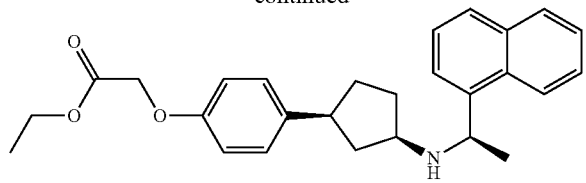

[4-((1R)-3-oxo-cyclopentyl)-phenoxy]-acetic acid ethyl ester (see WO2009/065406) (40.0 g, 153 mmol) and (R)(+)-1-naphthalen-1-yl-ethylamine (28.7 g, 168 mmol) was suspended in acetonitrile (1.4 l) and conc. acetic acid (87.2 ml). The clear orange solution was stirred for 1 hour at room temperature before NaBH(OAc)$_3$ (51.7 g, 244 mmol) was added in portions over 30 minutes. After 24 hours HPLC showed 12% remaining starting material and additional NaBH(OAc)$_3$ was added but still some starting material remained. The reaction mixture was poured into water and extracted with ethyl acetate. The organic phase was dried over MgSO$_4$ and concentrated in vacuo to give a light brown oil. The crude product was purified by column chromatography with a mixture of hexane, ethyl acetate, isopropanol and triethylamine (79:19:1.5:0.5) to give the desired diastereoisomer. Yield: 5.9 g. HPLC purity >96%.

HPLC conditions: flow=0.8; Column: Ascentis (R) Express C18; Eluent: 50% 0,025 M acetic acid, 50% acetonitrile pH=5.5

Step 2: Saponification of {4-[(1R,3S)-3-((R)-1-naphthalen-1-yl-ethylamino)-cyclopentyl]-phenoxy}-acetic acid ethyl ester to afford {4-[(1R,3S)-3-((R)-1-naphthalen-1-yl-ethyl-amino)-cyclopentyl]-phenoxy}-acetic acid

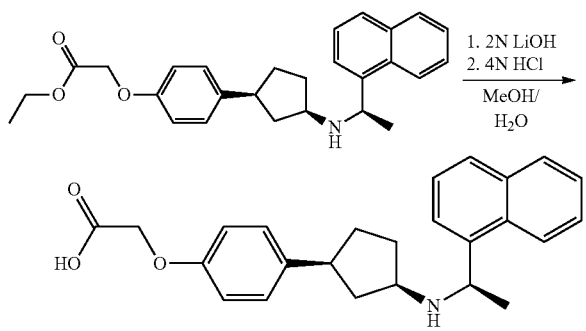

{4-[(1R,3S)-3-((R)-1-naphthalen-1-yl-ethylamino)-cyclopentyl]-phenoxy}-acetic acid ethyl ester (0.214 g, 0.51 mmol) was added to a mixture of methanol (2.35 ml) and water (0.78 ml). To the milk-white mixture was added aqueous 2N LiOH (2.05 ml, 4.1 mmol). After stirring for about 10 minutes at room temperature the reaction mixture changed into a clear light yellow solution. The solution was stirred overnight at room temperature. After 20 hours the solution was concentrated slightly in vacuo and further 5 ml of water was added. The product was precipitated by adding 4N HCl (2.4 ml) under vigorous stirring. pH was adjusted to 5 with aqueous 2N LiOH. The precipitate was collected by filtration to give crude amorphous {4-[(1R,3S)-3-((R)-1-naphthalen-1-yl-ethylamino)-cyclopentyl]phenoxy}-acetic acid. Yield: 0.19 g (95%).

Example 2

Crystallisation of Form X of {4-[(1R,3S)-3-((R)-1-Naphthalen-1-yl-ethylamino)-cyclopentyl]-phenoxy}-acetic acid 40 mg of amorphous compound (Example 1, above) were placed in a reaction vial for microwave oven and 1 mL of MeOH was added slowly during heating with a heat gun until all material had been dissolved. The hot solution was filtered with 0.45 μm syringe filter (the filter was heated to 50° C. before use), and then placed at 5° C. for slow formation of crystalline Form X.

Example 3

Two-step, one pot procedure for the crystallisation of Form X of {4-[(1R,3S)-3-((R)-1-Naphthalen-1-yl-ethylamino)-cyclopentyl]-phenoxy}-acetic acid directly from a saponification reaction mixture {4-[(1R,3S)-3-((R)-1-naphthalen-1-yl-ethylamino)-cyclopentyl]-phenoxy}-acetic acid ethyl ester (20 g, 47.9 mmol) was dissolved in ethanol (160 ml). 2N aqueous sodium hydroxide (160 ml) was added and the solution was stirred at room temperature overnight. The solution was concentrated to about ½ the volume in vacuo and water (130 ml) was added.

The pH was adjusted to about 5.3 with 50% acetic acid. After several hours of stirring at room temperature during which period the product slowly crystallizes, the reaction mixture was filtered, washed with water and dried in vacuum for two days. Yield: 17 g.

Example 4

XRC Single Crystal Structure of Form X of {4-[(1R,3S)-3-((R)-1-Naphthalen-1-yl-ethylamino)-cyclopentyl]-phenoxy}-acetic acid A representative crystal obtained by crystallisation from a diluted MeOH solution under slow evaporation conditions was surveyed and a 0.9 Å data set was collected at 120K on a Bruker Smart diffractometer. The crystal structure solution was found and refinement was performed using the SHELXTL-97 system. See, Sheldrick, G. M., 1990 and 1997.

Hydrogen atoms on fixed ideal positions were included. The shifts calculated in the final cycle of least squares refinement were all less than 0.1 of their corresponding standard deviations, and the final R index was 7.87%. A final difference Fourier revealed no missing or misplaced electron density.

Details of the crystal are provided by Table 1 above. Experimental details concerning the single crystal structure determination are provided by Table 2. Selected atomic coordinates, equivalent isotropic displacement parameter and site occupancy factors are provided in Table 3. Bond lengths and angles are provided in Table 4 and Table 5.

Example 5

Solubility Determination

The aqueous solubility of Form C and Form X was determined as a function of pH at 25° C. in 0.1N HCl (pH 1.0) and in Sorensen phosphate buffers at pH 2.0, 4.0, 6.0 and 8.0. For each pH value two individual determinations were made.

Form C or Form X was weighed out (11 mg for pH 1, 4 mg for pH 2-8) in scintillation vials and 4 ml 0.1N HCl or buffer was added. The vials were shaken for 24 hours at 25° C. After 24 hours it was checked that the vial still contained undissolved material. The suspensions were filtered through a 0.45 μm filter, which was first saturated with app. 0.5 ml filtrate. The resulting filtrates were diluted and analyzed by HPLC vs. a standard curve. The results are given in Table 6, from which it can be concluded that at room temperature the solubility of Form X is higher compared to Form C.

The invention claimed is:

1. A crystalline form of {4-[(1R,3S)-3-((R)-1-Naphthalen-1-yl-ethylamino)-cyclopentyl]-phenoxy}-acetic acid which has an X-ray powder diffraction pattern that exhibits characteristic peaks expressed in 2θ at approximately 8.0, 11.3, 11.4, 15.0, 18.2 and 21.5.

2. The crystalline form according to claim 1 which belongs to the orthorhombic space group $P2_12_12_1$ having unit-cell parameters a=8.7299(17) Å, b=14.822(3) Å and c=16.353(3) Å.

3. The crystalline form according to claim 1 which has an X-ray powder diffraction pattern that exhibits characteristic peaks expressed in 2θ at approximately within ±0.05 degrees of the listed peaks.

4. The crystalline form according to claim 1 which has an X-ray powder diffraction pattern substantially as appears from Graph 2b.

5. The crystalline form according to claim 1 which has a differential scanning calorimetry curve comprising an event with an onset at about 255° C. (12° C.).

6. The crystalline foam according to claim 1 which has a differential scanning calorimetry curve substantially as appears from Graph 4b.

7. The crystalline form according to claim 1 which has Solid State NMR spectrum substantially as appears from Graph 8b.

8. The crystalline form according to claim 1 which does not undergo any solid state transformation during 4 week stress stability testing at 60° C., 60° C./75% relative humidity and 80° C./75% relative humidity.

9. The crystalline form according to claim 1 which has an attenuated total reflectance Fourier transform infrared (ATR-FTIR) spectrum substantially as appears from Graph 6b.

10. The crystalline form according to claim 1, further characterized by an ATR-FTIR spectrum exhibiting attenuated total reflectance peaks at approximately 1409, 1113, 1061, 939, 841, and/or 701 ($\pm 3$ cm$^{-1}$).

11. The crystalline form according to claim 1 which has XRC single crystal parameters that are substantially the same as those provided in Table 2.

12. The crystalline form according to claim 11 which comprises atoms at atomic positions relative to the origin of the unit cell as set forth in Table 3 or bond lengths as set forth in Table 4 or bond angles as set forth in Table 5.

13. The crystalline form according to claim 11 which has a XRC single crystal structure according to Formula 2

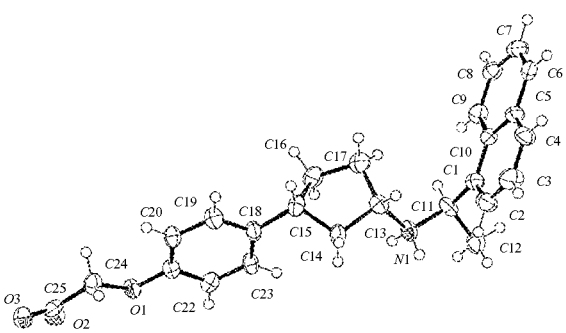

Formula 2

14. A process for preparing the crystalline form of {4-[(1R,3S)-3-((R)-1-Naphthalen-1-yl-ethylamino)-cyclopentyl]-phenoxy}-acetic acid which has an X-ray powder diffraction pattern that exhibits characteristic peaks expressed in 2θ at approximately 8.0, 11.3, 11.4, 15.0, 18.2 and 21.5, said process comprising the steps of either: . . . (the rest of the claim remains the same).

15. The process according to claim 14, wherein the X-ray diffraction pattern exhibits characteristic peaks expressed in 2θ at approximately within ±0.05 degrees of the listed peaks.

* * * * *